United States Patent [19]

Warner

[11] Patent Number: 4,834,107

[45] Date of Patent: May 30, 1989

[54] HEART-RELATED PARAMETERS MONITORING APPARATUS

[75] Inventor: Glenfield Warner, St. Laurent, Canada

[73] Assignees: Sylvia Warner, St. Laurent; Priyamvada Sankar, Brossard, both of Canada

[21] Appl. No.: 105,803

[22] Filed: Oct. 8, 1987

Related U.S. Application Data

[63] Continuation-in-part of Ser. No. 59,520, Jun. 8, 1987, which is a continuation-in-part of Ser. No. 807,693, Dec. 11, 1985, abandoned, which is a continuation-in-part of Ser. No. 608,955, May 10, 1984, abandoned.

[51] Int. Cl.$^4$ .................................................. A61B 5/02
[52] U.S. Cl. .................................... 128/668; 128/666; 128/691; 128/694; 128/713
[58] Field of Search ............... 128/668, 691, 694, 713, 128/666

[56] References Cited

U.S. PATENT DOCUMENTS 4,030,485 6/1977 Warner ......................... 128/2.05 A
4,425,920 1/1984 Bowland ............................ 128/672

FOREIGN PATENT DOCUMENTS 2092309 8/1982 United Kingdom ............... 128/672

Primary Examiner—Asok Pal
Attorney, Agent, or Firm—Chilton, Alix & Van Kirk

[57] ABSTRACT

A non-invasive method, and an apparatus, for determining heart-related parameters in patients. The method and apparatus determine pulse pressure, time constant of the arterial system, systolic and diastolic pressure, peripheral resistance, cardiac output and mean arterial blood pressure.

16 Claims, 6 Drawing Sheets

HEART-RELATED PARAMETERS MONITORING APPARATUS

CROSS-REFERENCE TO RELATED APPLICATIONS

This application is a continuation-in-part application Ser. No. 059,520, filed June 8, 1987, which is a continuation-in-part application Ser. No. 807,693, filed Dec. 11, 1985, now abandoned which is a continuation-in-part of parent application Ser. No. 608,955, filed May 10, 1984, now all abandoned.

BACKGROUND OF INVENTION

1. Field of the Invention

The invention relates to a non-invasive method of measuring arterial blood pressure and cardiac output. The invention also relates to an apparatus for carrying out the method.

2. Description of Prior Art

Non-invasive methods and apparatus for measuring arterial blood pressure and cardiac output are known in the art. Once such method and apparatus is illustrated in U.S. Pat. No. 4,030,485, Warner, issued June 21, 1977. A second such method and apparatus is taught in U.S. Pat. No. 4,418,700, Warner, issued Dec. 6, 1983. The present invention constitutes an improvement and refinement of the method and apparatus as taught in the latter patent.

SUMMARY OF INVENTION

The invention relates to a non-invasive method, and an apparatus for determining heart-related parameters in patients. The method and apparatus determine pulse pressure, time constant of the arterial system, systolic and diastolic pressure, peripheral resistance, and cardiac output and means arterial blood pressure.

BRIEF DESCRIPTION OF DRAWINGS

The invention will be better understood by an examination of the following description together with the accompanying drawings in which.

DESCRIPTION OF PREFERRED EMBODIMENTS

Figure 1:
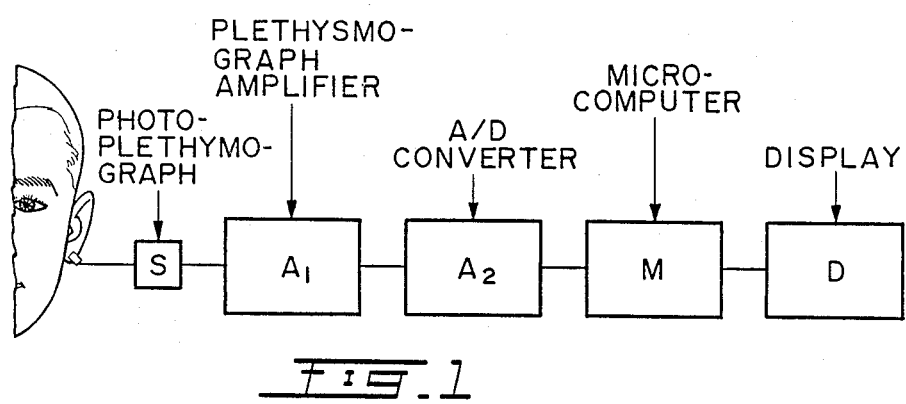
FIG. 1 is a block diagram of the apparatus for carrying out the inventive method.

As seen in FIG. 1, an apparatus in accordance with the invention comprises a volume sensor such as a photo-electric plethysmograph S, an amplifier $A_1$, an analog to digital converter $A_2$, a microcomputer M and a display device D. The plethysmograph sensor S is attached to, for example, the earlobe of a subject. The sensor could also be attached to other suitable parts of the body such as the forehead, fingertips or toes.

Figure 2:
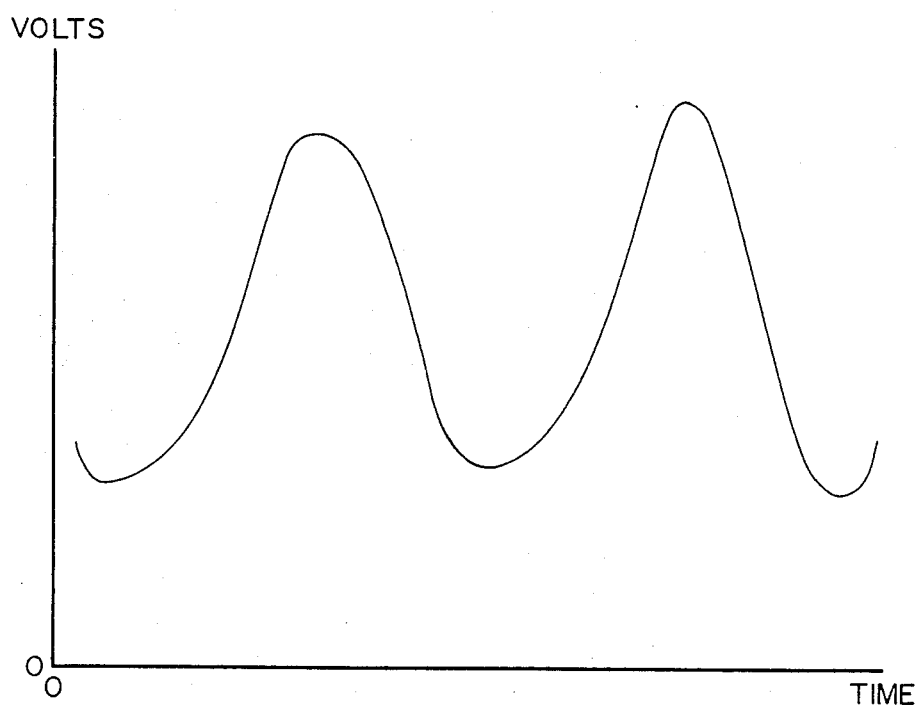
FIG. 2 is a typical sensor output of the system as illustrated in FIG. 1.

As is known, the plethysmograph, detects changes in blood volume of the region to which it is attached. A typical sensor output signal is shown in FIG. 2. As seen in FIG. 2, the output signal has a pulsating component and a DC component.

The output of the sensor is applied to the plethysmograph amplifier $A_1$ where it is amplified and filtered and the DC component is discarded. The output of $A_1$ has a DC component, but this is not directly related to the sensor DC component.

The output of $A_1$ is fed to the analog to digital (A/D) converter $A_2$ which digitizes the signal. In a preferred embodiment, the sampling rate is 100 per second.

Figure 6:
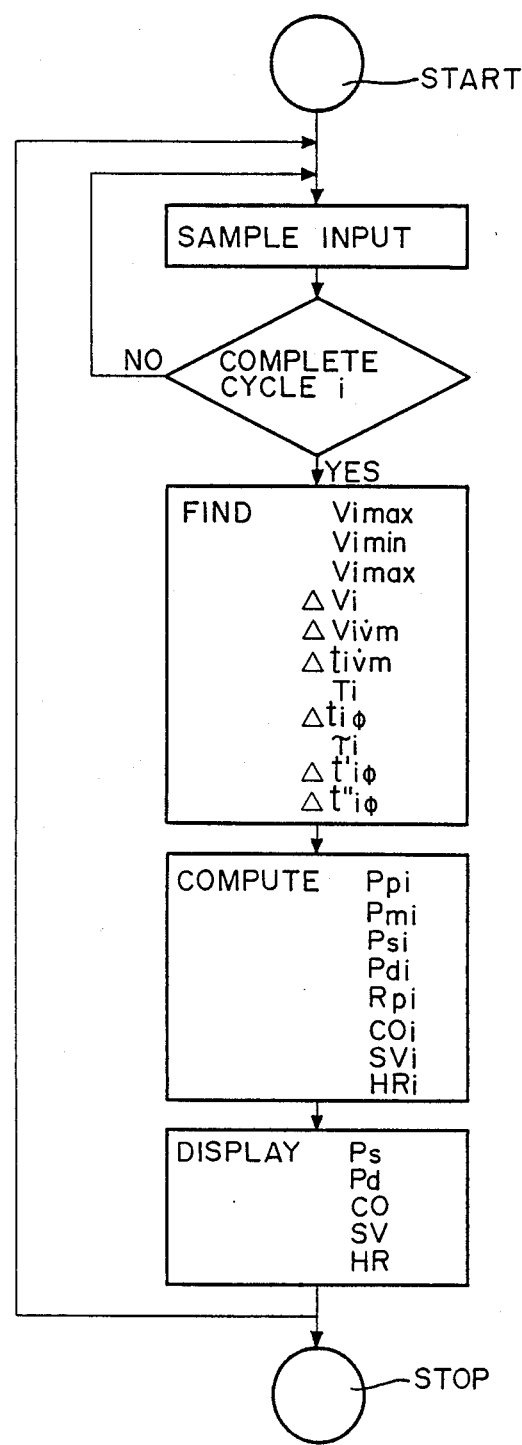
FIG. 6 is a simplified flowchart for a computer program for performing calculations in accordance with the invention.

Microcomputer M accepts signals from $A_2$ and processes them according to the instructions it contains. These instructions are schematically represented in the simplified flowchart of FIG. 6.

The computer quantities are then displayed on a CRT monitor D or other suitable display means.

THEORY

Figure 3:
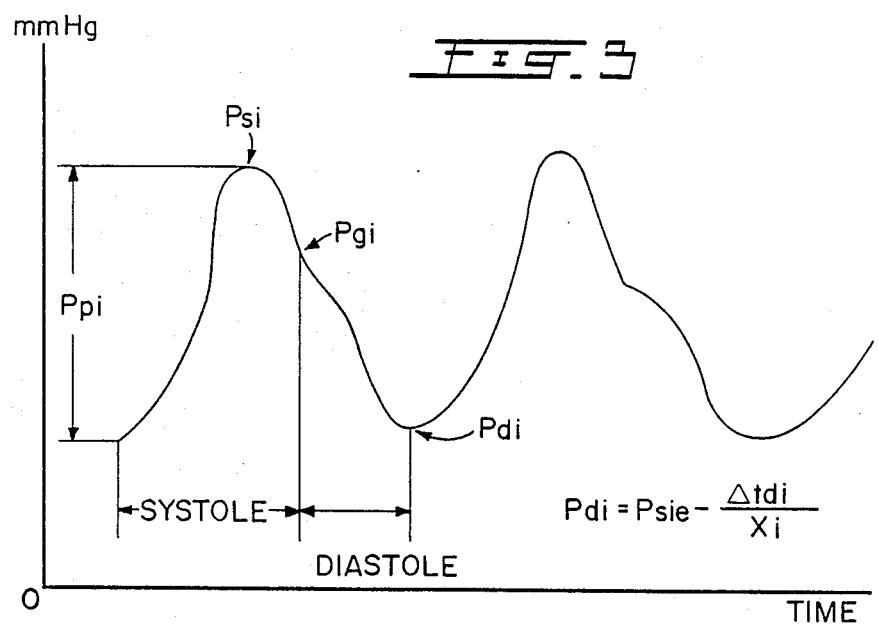
FIG. 3 illustrates arterial blood pressure pulses.
Figure 5:
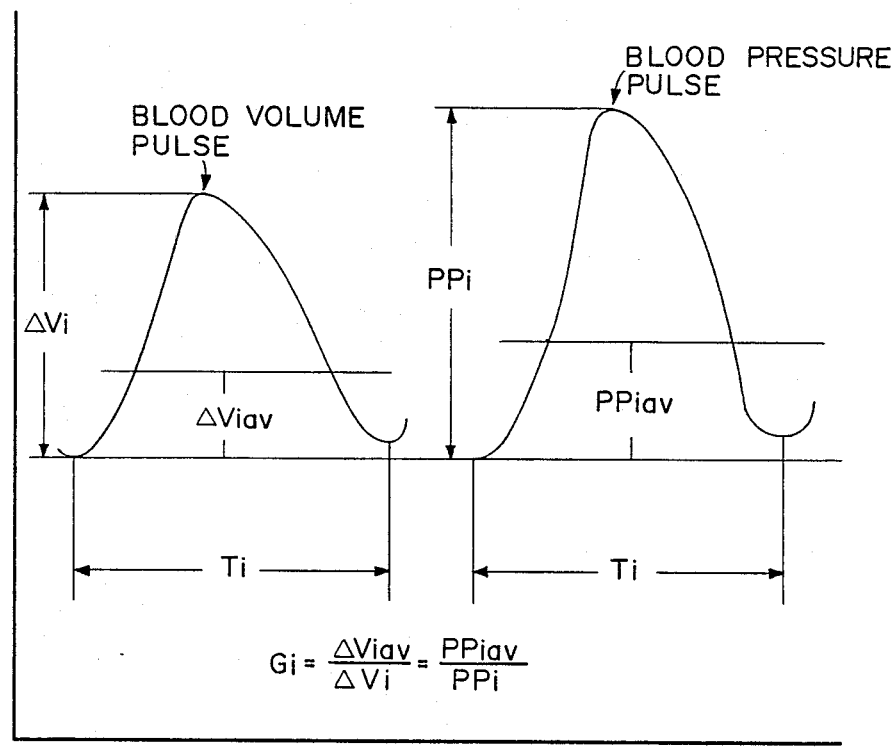
FIG. 5 illustrates a blood volume pulse and a blood pressure pulse to illustrate the ratio g.

Arterial blood pressure pulses are shown in FIG. 3. The shape of these curves vary according to the site where they are measured. The highest pressure reached during a cycle i is called the arterial systolic blood pressure, $P_{si}$. The lowest pressure reached during the same cycle is called the arterial diastolic blood pressure, $P_{di}$. The pressure rise from $P_{di}$ to $p_{si}$ in the same cycle is the pulse pressure, $p_{pi}$.

By definition $$p_{si} - p_{di} = p_{pi} \tag{1}$$

To find $P_{pi}$

Figure 4:
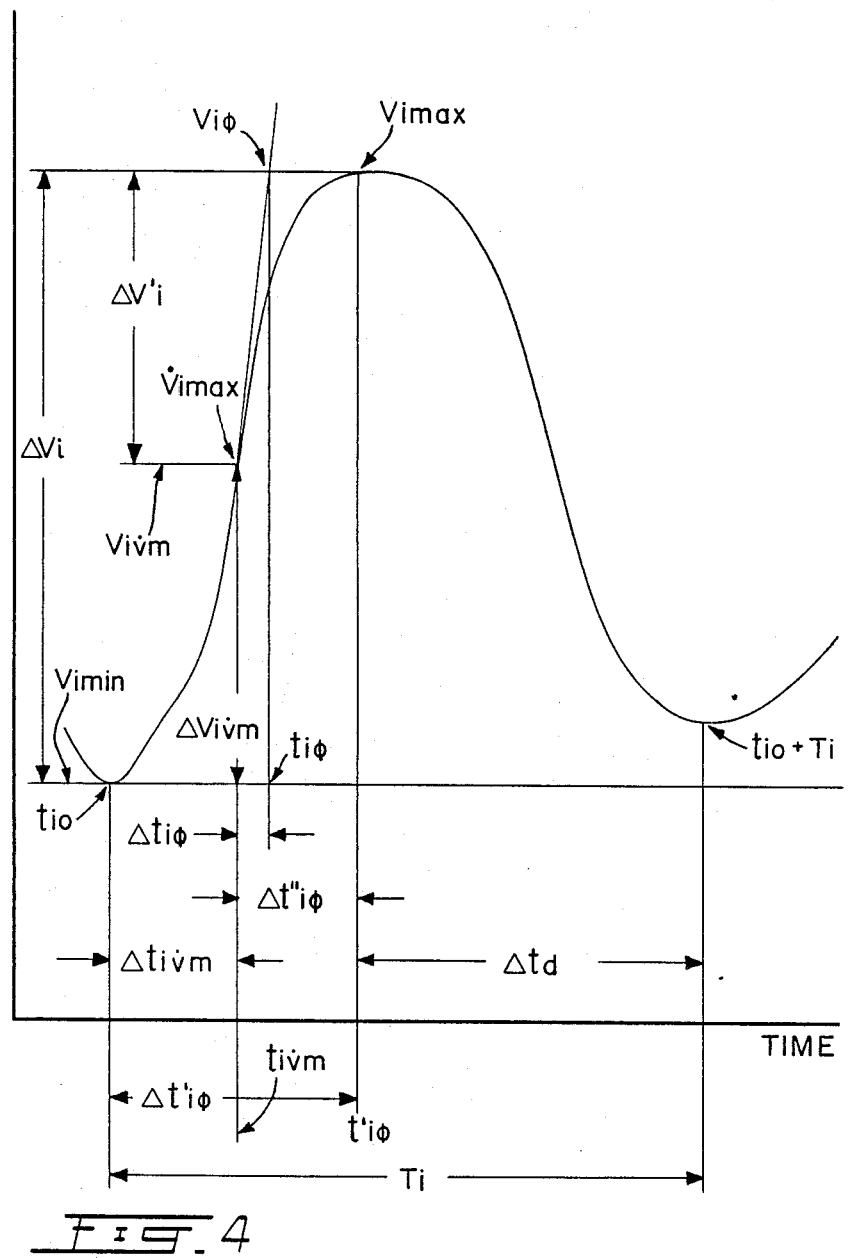
FIGS. 4, 4a and 4b illustrate a blood volume pulse.
Figure 4A:
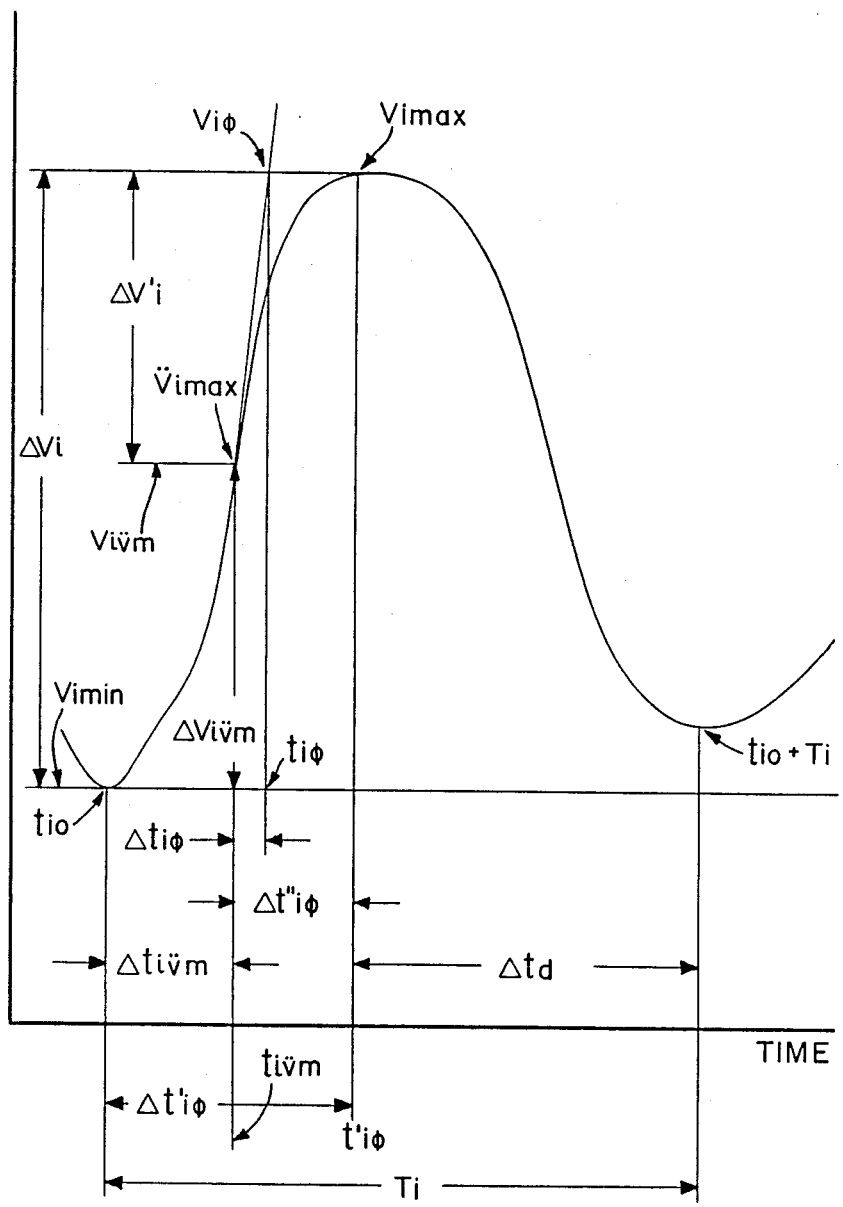

A plethysmographic pulse is shown in FIG. 4. The minimum value at the beginning of the pulse is $V_{imin}$. The maximum value of the pulse is $V_{imax}$. As the pulse volume rises from $V_{imin}$ to $V_{imax}$, the time rate of volume change reaches a maximum $\dot{V}_{imax}$ at time $t_i\dot{v}_m$. The pulse volume at time $t_i\dot{v}_m$ is $V_{i\dot{v}_m}$.

let $$\frac{V_{i\dot{v}_m} - V_{imin}}{V_{imax} - V_{imin}} = \frac{\Delta V_{i\dot{v}_m}}{\Delta V_i} = R_i \tag{2}$$

In addition to finding the values of $V_{i\dot{v}_m}$ corresponding to $\dot{V}_{imax}$, see U.S. Pat. No. 4,418,700, Warner, values of $V_{i\dot{v}_m}$ are also found corresponding to $\dot{V}_{imax}-1$, $\dot{V}_{imax}-2, \ldots \dot{V}_{imax}-k$, where k is a function of $\dot{V}_{imax}$.

All of the values of $\dot{V}_{iVm}$ corresponding to the time rates of volume change lying between and including $\dot{V}_{imax}$ and $\dot{V}_{imax}-k$ are averaged and used to compute $\Delta V_{i\dot{v}_m}$.

The average value of $V_{iV}m$ is $$\overline{V}_{i\dot{v}m} = \frac{\sum_{1}^{n0} V_{i\dot{v}_0mn0} + \sum_{1}^{n1} V_{i\dot{v}_1mn1} + \ldots + \sum_{1}^{nk} V_{i\dot{v}_kmnk}}{n0 + n1 + \ldots + nk}$$

where n0 = number of values of $V_{i\dot{v}_0}m$ corresponding to $\dot{V}_{imax}$ n1 = number of values of $V_{i\dot{v}_1m}$ corresponding to $\dot{V}_{imax} - 1$

... = ...

nk = number of values of $V_{i\dot{v}_k}m$ corresponding to $\dot{V}_{imax}-k$ $k = (\dot{V}_{imax}/m)$ (integral values only) +1 m = constant ... a preferred value of m = 20
l = constant ... a preferred value of l = 1

$$P_{pi} = K_{pp}\left(\frac{R_i - r_1}{(1 + r_2 - R_i)}\alpha\right) \quad (4a)$$

$K_{pp}$ = constant determined by a first calibration
$r_1$ = constant ... preferably equal to 0
$r_2$ = constant ... preferably equal to 0
$0 \leq \alpha \leq 1$
$R_{i1}$ can now be defined, as per equation (2) above, but using the average value of $V_{iVm}$ so that equation (2) can be rewritten $$\text{let } \frac{\overline{V_iV_m} - V_{imin}}{V_{imax} - V_{imin}} = \frac{\Delta V_iV_m}{\Delta V_i} = R_i \quad (2)$$

From FIG. 4

$\Delta V'_i = \Delta V_i - \Delta V_{ivm}$ $$\frac{\Delta V'_i}{\Delta V_i} = R' = \frac{\Delta V_i - \Delta V_{ivm}}{\Delta V_i} = 1 - \frac{\Delta V_{ivm}}{\Delta V_i} = 1 - R_i$$

wherein $R'_i = 1 - R_i$ or $R_i = 1 - R'_i$

No other calibration should be required with different subjects. However, if desired, $K_{pp}$ can be determined for each subject.

To find mean blood pressure

The mean blood pressure $P_{mi}$ during a cycle i is given by $$P_{mmi} = K_4\left[\frac{\Delta V_i}{\Delta \dot{V}_{imax}}\right]^{-b_3} \quad (5)$$

$P_{mi} = P_{mmi} + P_0 \quad (6)$ $b_3$ = exponent ... the preferred value of $b_3$ is equal to 0.5
$K_4$ = constant determined at calibration for each subject. It is only necessary to find this constant once for each subject. The measurements carried out at different times on the same subject do not require separate calibration
$P_0$ = constant ... preferred 25 mmHg $\Delta \dot{V}_{imax}$ = maximum time rate of change of $\Delta V_i$
       = $\dot{V}_{imax}$ $P_{si} = P_{mi} + (1 - g_i)P_{pi} \quad (7)$ where
$g_i = (\Delta V_{iAV}/\Delta V_i)$
$\Delta V_{iAV}$ = average value of $\Delta V_i$ over the time interval $T_i$ $P_{di} = P_{si} - P_{pi} \quad (8)$ The variable $g_i$ can take on a constant value $g_0$ whose preferred value is 0.333.

Alternatively, mean blood pressure can be determined using the following expression:

$$P_{mmi} = K_4\left[\frac{\Delta V_i}{\Delta \dot{V}_{imax}[G(t)]}\right]^{-b_3} \quad (5')$$

$$= K_4\left(\frac{1}{r_i}\right)^{-b_3}$$

(For definition of $r_i$, see Equation (10) below).

where
$G(t)$ = a function of t, in a particular case,
$G(t) = (\phi_c/\phi_i)$
$\phi_c = ((1/\Delta t_c))^Y$
$\phi_i = ((1/\Delta t_i))^Y$
$\Delta t_c = (\Delta t'_{i\phi c}$
$\Delta t_i = \Delta t'_{i\phi}$ where
$T_c$ = T at calibration
$t_c$ = t at calibration $\Delta t'_{i\phi c}$ (see FIG. 4B)
$\phi_c = (T_c/t_c) = (T/t)$ at calibration
$y$ = constant The remainder of the terms in equation 5' are the same as similar terms in equation 5.

Figure 4B:
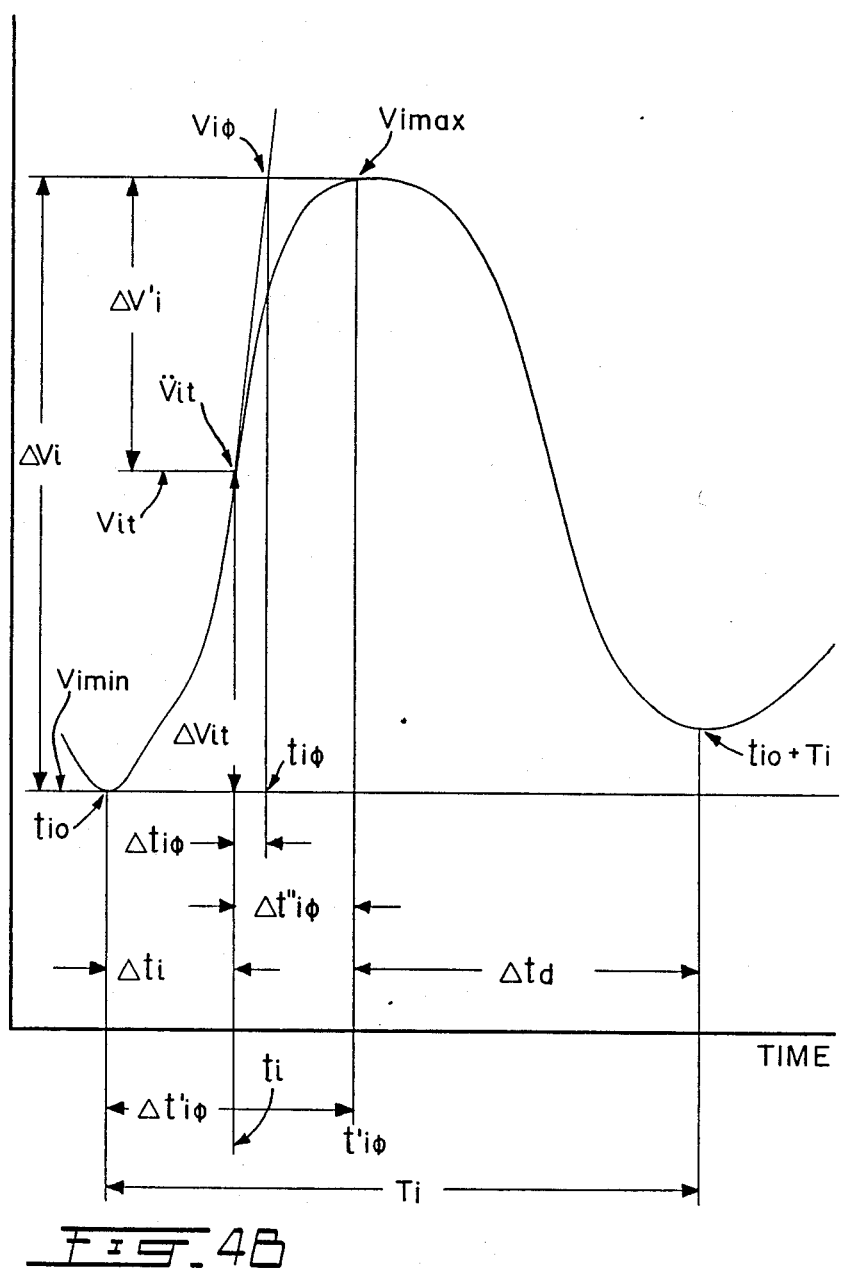

Determination of ratio R (FIG. 4b)
From FIG. 4b, the ratio R is $R_i = (\Delta V_{it}/\Delta V_i)$ where
$\Delta V_{it}$ = change in volume at predetermined time ti
$\Delta V_i$ = total volume change during cycle i
$t_i$ = time such that $\Delta t_i = K_T \Delta t'_{i\phi}$
$K_T$ = constant Estimation of pulse pressure, PP $$\frac{1 - e^{-K'T_k PP_i}}{1 - e^{-kPP_i}} = R_i$$

where
$PP_i$ = pulse pressure = $p_s - P_d$
$P_s$ = systolic blood pressure
$P_d$ = diastolic blood pressure
k = constant
$K'_T$ = constant $\simeq K_T$ In FIG. 4B $\Delta V'_i = \Delta V_i - \Delta V_{it}$ $$\frac{\Delta V'_i}{\Delta V_i} = \frac{\Delta V_i - \Delta V_{it}}{\Delta V_i} = 1 - \frac{\Delta v_{it}}{\Delta V_i} = 1 - R_i = R'_i$$

wherein from the above equation:

$$1 - \frac{1 - e^{-K_Tk PP_i}}{1 - e^{-kPP_i}} = 1 - R_i$$

$$\frac{1 - e^{-kPP_i} - (1 - e^{-K_Tk PP_i})}{1 - e^{-kPP_i}} = 1 - R_i$$

-continued
$$\frac{-e^{-kPP_i} + e^{-KTkPP_i}}{1 - e^{-kPP_i}} = 1 - R_i$$

multiply numerator and denominator by $e^{kPP_i}$ $$\frac{-1 + e^{kPP_i} e^{-KTkPP_i}}{e^{kPP_i} - 1} = 1 - R_i$$

$$\frac{e^{kPP_i(1-KT)} - 1}{e^{kPP_i} - 1} = 1 - R_i = R'_i.$$

Determination of r
From FIG. 4

$$r_i = (\dot{V}_{imax}/\Delta V_i)G(t)$$

where
$\dot{V}_{imax}$ = maximum time rate of volume increase in cycle i
$\Delta V_i$ = total volume increase during cycle i
From FIG. 4b $$r_i = (\dot{V}_{it}\Delta V_i)G(t)$$

where
$\dot{V}_{it}$ = time rate of increase of volume $V_{i(t)}$ at time $t_i$
$\Delta V_i$ = total volume increase of volume during
Estimation of Mean Blood Pressure
(1) $P_{mi}' = K_1 r_{ic}{}^a$
$K_1$ = calibration constant
$P_{mi}' = (P_s + P_d)/2 - P_o$ $P_{si}$ = systolic blood pressure, in cycle i
$P_{mi} = (P_s + P_d)/2$ $P_{di}$ = diastolic blood pressure, in cycle i
a = constant
$P_o$ = constant
(2) $e^{kPmi} = K_2 R_{ic}{}^b$
where
$K_2$ = constant (calibration)
b = constant $$(K_3)\frac{e^{-k(Pmo-j\phi_{1i})} - e^{-k(Pmo+\phi_{2i})}}{e^{-k(Pmo-\phi_{1i})} - e^{-k(Pmo+\phi_{2i})}} = r_i \quad (9)$$

where
$P_{mo}$ = constant at calibration
$\phi_{1i} + \phi_{2i} = PP_i$ = pulse pressure during cycle i
k = constant
j = constant
solve equation by making LHS=RHS by varying $\phi_{1i}$ and $\phi_{2i}(\phi_{2i} = PP_i - \phi_{1i})$
then
$P_{si} = P_{mo} + \phi_{2i} + P_0$
$P_{di} = P_{mo} - \phi_{1i} + P_o$
$P_{mi} = (P_{si} + P_{di})/2$
$P_0$ = constant
$r_i$ = ratio of exponentials
$K_3$ = coefficient (variable or constant)
Correction for $r_i$
$r_i$ (corrected) = $r_{ic} = r_i e^{m(\phi_o - \phi_i)}$
m = constant
$\phi_0 = PP_i$ at calibration
$\phi_i$ = current value of $PP_i$.
Equation (9) above is only one form which this particular equation can take. By simple mathematical manipulations, the invention may take two other forms as per (10) and (11) below. What follows is the manipulations as well as the two other forms of the equation:
As above noted $$\phi_{2i} + \phi_{1i} = PP_i = P_{si} - P_{di}$$

$$\phi_{2i} + \phi_{1i} = (P_{si} - P_o) - (P_{di} - P_o)$$

Let
$P'_{si} = P_{si} - P_o$ $p'_{di} = P_{di} - P_0$ $\phi_{2i} + \phi_{1i} = P'_{si} - P'_{di}$
add and subtract $P_{mo}$ on RHS above $$\phi_{2i} + \phi_{1i} = P'_{si} - P_{mo} + P_{mo} - P'_{di} \quad (A)$$

$\phi_{2i}$ and $\phi_{1i}$ can take on any values in satisfying the above equation (A)
Put $\phi_{2i} = P'_{si} - P_{mo}$
and $\phi_{1i} = P_{mo} - P'_{di}$ in equation (9)
then $$K_3\left[\frac{e^{-k(Pmo-j(Pmo-P'di))} - e^{-k(Pmo+j(P'si-Pmo))}}{e^{-k(Pmo-(Pmo-P'di))} - e^{-k(Pmo+(P'si-Pmo))}}\right] = r_i \quad (10)$$

simplifying the denominator $$K_3\left[\frac{e^{-k(Pmo-j(Pmo-P'di))} - e^{-k(Pmo+j(P'si-Pmo))}}{e^{-kP'di} - e^{-kP'si}}\right] = r_i \quad (11)$$

To solve equation 11:
(1) Set $P'_{di} = P'_{si} - PP_i$ and solve for $P'_{si}$
(2) Set $P'_{si} = P'_{di} - PP_i$ and solve for $P'_{di}$
Although particular embodiments have been illustrated, this was for the purpose of describing, but not limiting, the invention. Various modifications, which will come readily to the mind of one skilled in the art, are within the scope of the invention as defined in the appended claims.

I claim:
1. Apparatus for determining the magnitude of heart-related parameters in a patient;
comprising;
means for detecting blood volume, and thereby blood volume variation, in said patient, and for providing a signal representative of said blood volume, and thereby said blood volume variation;
said means for detecting being attachable to said patient to thereby detect said blood volume, and thereby said blood volume variation;
said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum aplitude, said maximum rate of change of said signal, said first difference, said second different, said first time interval, and said second time interval; and means for calculating the magnitude of selected ones of said parameters, said means for calculating being connected to both said means for detecting and means for measuring;

wherein means for calculating calculates the magnitude of the pulse pressure parameter in accordance with the following expression;

$$P_{pi} = K_{pp} \left[ \frac{R_{il} - r_1}{(1 + r_2 - R_{il})} \right]$$

wherein
$P_{pi}$ = pulse pressure during cycle i
$K_{pp}$ = constant determined by a first calibration
$r_1$ = constant
$r_2$ = constant
$R_{il} = (\Delta V_i \dot{V}_m / \Delta V_i)$
  where $\Delta V_i \dot{V}_m$ = volume change at time $t_{iVm}$ during cycle i corresponding to maximum rate of volume change, $\dot{V}_{imax}$
  $\Delta V_i$ = maximum volume change during cycle i
  $\Delta t_{i\dot{V}m}$ = time interval from start of cycle i to time of maximum rate of volume change $\dot{V}_{imax}$.

2. Apparatus for determining the magnitude of heart-related parameters in a patient; comprising;

means for detecting blood volume, and thereby blood volume variation, in said patient, and for providing a signal representative of said blood volume, and thereby said blood volume variation;

said means for detecting being attachable to said patient to thereby said blood volume, and thereby said blood volume variation;

said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum aplitude, said maximum rate of change of said signal, said first difference, said second different, said first time interval, and said second time interval; and means for calculating the magnitude of selected ones of said parameters, said means for calculating being connected to both said means for detecting and means for measuring;

wherein means for calculating calulates the magnitude of the mean arterial blood pressure, $P_{mi}$ parameter in accordance with the following expression:

$$P_{mi} = P_0 + P_{mmi}$$

$$P_{mmi} = K_4 \left[ \frac{\Delta V_i}{\Delta \dot{V}_{imax} [G(t)]} \right] - b_3$$

where
$K_4$ = constant determined for each subject
$b_3$ = constant
$P_{mmi}$ = pseudo mean arterial blood pressure during cycle i
$\Delta_i$ = maximum volume change during cycle i $\Delta \dot{V}_{imax}$ = maximum time rate of change of $\Delta V_i$
$\phantom{\Delta \dot{V}_{imax}}$ = $\dot{V}_{imax}$ where $$G(t) = \frac{\phi_c}{\phi_i}$$

$$\phi_c = \left[ \frac{1}{\Delta t_c} \right]^y$$

$$\phi_i = \left[ \frac{1}{\Delta t_i} \right]^y$$

where $\Delta t_c = \Delta t$ at calibration = $\Delta t_{i\phi c}$ $\Delta t_i = \Delta t_{i\phi}$ $y$ = constant.

3. Apparatus for determining the magnitude of heart-related parameters in a patient; comprising;

means for detecting blood volume, and thereby blood volume variation, in said patient, and for providing a signal representative of said blood volume, and thereby said blood volume variation;

said means for detecting being attachable to said patient to thereby detect said blood volume, and thereby said blood volume variation;

said volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum aplitude, said maximum rate of change of said signal, said first difference, said second different, said first time interval, and said second time interval; and means for calculating the magnitude of selected ones of said parameters, said means for calculating being connected to both said means for detecting and means for measuring;

wherein means for calculating calculates the magnitude of the systolic pressure ($P_{si}$) parameter in accordance with the following expression:

$$P_{si} = P_{mi} + (1 - g_0)P_{pi}$$

wherein
$g_0$ = constant.

4. Apparatus for determining the magnitude of heart-related parameters in a patient;
comprising:

means for detecting blood volume, and thereby blood volume variation, in said patient, and for providing a signal representative of said blood volume, and thereby said blood volume variation;

said means for detecting being attachable to said patient to thereby detect said blood volume, and thereby said blood volume variation;

said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum aplitude, said maximum rate of change of said signal, said first difference, said second different, said first time interval, and said second time interval; and means for calculating the magnitude of selected ones of said parameters, said means for calculating being connected to both said means for detecting and means for measuring;

wherein means for calculating calculates the magnitude of the systolic pressure ($P_{si}$) parameter in accordance with the following expression:

$$P_{si} = P_{mi} + (1 - g_i)P_{pi}$$

wherein:
$g_i = (\Delta V_{iAV}/\Delta V_i)$
$P_{pi}$ = pulse pressure during cycle i
$\Delta V_i$ = represented by said first difference
$\Delta V_{iAV}$ = represented by the difference between said minimum amplitude and an amplitude equal to the average value of a pulse in a cycle i.

5. Apparatus for determining the magnitude of heart-related parameters in a patient;
comprising;

means for detecting blood volume, and thereby blood volume variation, in said patient, and for providing a signal representative of said blood volume, and thereby said blood volume variation;

said means for detecting being attachable to said patient to thereby detect said blood volume, and thereby said blood volume variation;

said blood volume variation being cycle in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum aplitude, said maximum rate of change of said signal, said first difference, said second different, said first time interval, and said second time interval; and means for calculating the magnitude of selected ones of said parameters, said means for calculating being connected to both said means for detecting and means for measuring;

wherein means for calculating calculates the magnitude of the arterial blood pressure, $P_{mi}$ parameter in accordance with the following expression:

$$P_{mi} = P_o + P_{mmi}$$

$$P_{mmi} = K_4 \left[ \frac{\Delta V_i}{\dot{V}_{imax} [G(t)]} \right] - b_3$$

where
 $K_4$ = constant determined for each subject
 $b_3$ = constant
 $P_{mmi}$ = pseudo mean arterial blood pressure during cycle i
 $\Delta V_i$ = maximum volume change during cycle i $\dot{V}_{imax}$ = maximum time rate of change of $V_i$
 = $\dot{V}_{imax}$ $P_o$ = constant
where
 $G(t)$ = a function of t.

6. A method for determining the magnitude of heart-related parameters in a patient;
comprising:
 detecting blood volume, and thereby blood volume variation, in said patient and providing a signal representative of said blood volume, and thereby said blood volume variation;
 said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and said minimum amplitude, a maximum rate of change of said signal being representative of the maximum rate of change of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;
 measuring said maximum amplitude, said minimum amplitude, said maximum rate of change of said signal, said first difference, said second difference, said first time interval, and said second time interval; and
 calculating the magnitude of the pulse pressure parameter in accordance with the following expression:

$$P_{pi} = K_{pp} \left[ \frac{R_{il} - r_1}{(1 + r_2 - R_{il})} \right]$$

wherein
 $P_{pi}$ = pulse pressure during cycle i
 $K_{pp}$ = constant determined by a first calibration
 $r_1$ = constant
 $r_2$ = constant
 $R_{il} = (\Delta V_i \dot{V}_m / \Delta V_i)$
 where
  $\Delta V_{i\dot{V}m}$ = volume change at time $t_{i\dot{V}m}$ during cycle i corresponding to maximum rate of volume change, $\dot{V}_{imax}$
  $\Delta V_i$ = maximum volume change during cycle i
  $\Delta t_{i\dot{V}m}$ = time interval from start of cycle i to time of maximum rate of volume change $\dot{V}_{imax}$.

7. A method for determining the magnitude of heart-related parameters in a patient;
comprising:
 detecting blood volume, and thereby blood volume variation, in said patient and providing a signal representative of said blood volume, and thereby said blood volume variation;
 said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and said minimum amplitude, a maximum rate of change of said signal being representative of the maximum rate of change of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;
 measuring said maximum amplitude, said minimum amplitude, said maximum rate of change of said signal, said first difference, said second difference, said first time interval, and said second time interval; and
 calculating the magnitude of the mean artial pressure $P_{mi}$ in accordance with the following expression:

$$P_{mi} = P_o + P_{mmi}$$

$$P_{mmi} = K_4 \left[ \frac{\Delta V_i}{\Delta \dot{V}_{imax} [G(t)]} \right] - b_3$$

where
K$_4$=constant determined for each subject
b$_3$=constant
P$_{mmi}$=pseudo mean arterial blood pressure during cycle i
$\Delta V_i$=maximum volume change during cycle i
$\Delta \dot{V}_{imax}$=maximum time rate of change of $\Delta V_i = \dot{V}_{imax}$ where $$G(t) = \frac{\phi_c}{\phi_i}$$

$$\phi_c = \left[ \frac{1}{\Delta t_c} \right]^y$$

$$\phi_i = \left[ \frac{1}{\Delta t_i} \right]^y$$

where $\Delta t_c = \Delta t$ at calibration $= \Delta t_{i\phi c}$ $\Delta t_i = \Delta t_{i\phi}$ y = constant.

8. A method for determining the magnitude of heart-related parameters in a patient; comprising:
  detecting blood volume, and thereby blood volume variation, in said patient and providing a signal representative of said blood volume, and thereby said blood volume variation;
  said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and said minimum amplitude, a maximum rate of change of said signal being representative of the maximum rate of change of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;
  measuring said maximum amplitude, said minimum amplitude, said maximum rate of change of said signal, said first difference, said second difference, said first time interval, and said second time interval; and
  calculating the magnitude of the systolic pressure (P$_{si}$ parameter in accordance with the following expression:

$P_{si} = P_{mi} + (1 - g_0)P_{pi}$ wherein
g$_0$=constant.

9. A method for determining the magnitude of heart-related parameters in a patient; comprising:
  detecting blood volume, and thereby blood volume variation, in said patient and providing a signal representive of said blood volume, and thereby said blood volume variation;
  said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and said minimum amplitude, a maximum rate of change of said signal being representative of the maximum rate of change of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;
  measuring said maximum amplitude, said minimum amplitude, said maximum rate of change of said signal, said first difference, said second difference, said first time interval, and said second time interval; and
  calculating the magnitude of the systolic pressure (P$_{si}$) parameter in accordance with the following expression:

$P_{si} = P_{mi} + (1 - g_i)P_{pi}$ wherein:
g$_i$=($\Delta V_{iAV}/\Delta V_i$)
P$_{pi}$=pulse pressure during cycle i
$\Delta V_i$=represented by said first difference
$\Delta V_{iAV}$=represented by the difference between said minimum amplitude and an amplitude equal to the average value of a pulse in a cycle i.

10. A method for determining the magnitude of heart-related parameters in a patient; comprising:
  detecting blood volume, and thereby blood volume variation, in said patient and providing a signal representative of said blood volume, and thereby said blood volume variation;
  said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and said minimum amplitude, a maximum rate of change of said signal being representative of the maximum rate of change of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;

measuring said maximum amplitude, said minimum amplitude, said maximum rate of change of said signal, said first difference, said second difference, said first time interval, and said second time interval; and calculating the magnitude of the arterial blood pressure, $P_{mi}$ parameter in accordance with the following expression:

$$P_{mi} = P_o + P_{mmi}$$

$$P_{mmi} = K_4 \left[ \frac{\Delta V_i}{\Delta \dot{V}_{imax}[G(t)]} \right] - b_3$$

where
$K_4$ = constant determined for each subject
$b_3$ = constant
$P_{mmi}$ = pseudo mean arterial blood pressure during cycle i
$\Delta V_i$ = maximum volume change during cycle i
$\Delta \dot{V}_{imax}$ = maximum time rate of change of $V_i = \dot{V}_{imax}$
$P_o$ = constant
$G(t)$ = a function of t and T.

11. Apparatus for determining the magnitude of heart-related parameters in a patient;
comprising:
means for detecting blood volume, and thereby blood volume variation, in said patient, and for providing a signal representative of said blood volume, and thereby said blood volume variation;
said means for detecting being attachable to said patient to thereby detect said blood volume, and thereby said blood volume variation;
said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum aplitude, said maximum rate of change of said signal, said first difference, said second different, said first time interval, and said second time interval; and means for calculating the magnitude of selected ones of said parameters, said means for calculating being connected to both said means for detecting and means for measuring;

wherein means for calculating calculates the magnitude of the pulse pressure parameter in accordance with the following expression:

$$P_{pi} = K_{pp} \left( \frac{R_{il} - r_1}{(1 + r_2 - R_{il})} \right)$$

wherein
$P_{pi}$ = pulse pressure during cycle i
$K_{pp}$ = constant determined by a first calibration
$r_1$ = constant
$r_2$ = constant
$R_{il} = \Delta V_i \dot{V}_m / \Delta V_i$
where
$\Delta V_i \dot{V}_m$ = volume change at preselected time $t_{i\dot{V}m}$ during cycle i
$\Delta V_i$ = maximum volume change during cycle i
$\Delta t_i \dot{V}_m$ = time interval from start of cycle i to preselected time of $t_{i\dot{V}m}$.

12. A method for determining the magnitude of heart-related parameters in a patient;
comprising:
detecting blood volume, and thereby blood volume variation, in said patient and providing a signal representative of said blood volume, and thereby said blood volume variation;
said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and said minimum amplitude, a maximum rate of change of said signal being representative of the maximum rate of charge of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;

measuring said maximum amplitude, said minimum amplitude, said maximum rate of change of said signal, said first difference, said second difference, said first time interval, and said second time interval; and calculating the magnitude of the pulse pressure parameter in accordance with the following expression:

$$P_{pi} = K_{pp}\left[\frac{R_{il} - r_1}{(1 + r_2 - R_{il})}\right]$$

wherein
$P_{pi}$ = pulse pressure during cycle i
$K_{pp}$ = constant determined by a first calibration
$r_1$ = constant
$r_2$ = constant
$R_{il} = (\Delta V_{i\dot{V}m}/V_i)$
where
$\Delta V_{i\dot{V}m}$ = volume change at preselected time $t_{i\dot{V}m}$ during cycle i
$\Delta V_i$ = maximum volume change during cycle i
$\Delta t_{i\dot{V}m}$ = time interval from start of cylcle i to predetermined time of $t_{i\dot{V}m}$.

13. Apparatus for determining the magnitude of heart-related parameters in a patient; comprising;

means for detecting blood volume, and thereby blood volume variation, in said patient, and for providing a signal representative of said blood volume, and thereby said blood volume variation;

said means for detecting being attachable to said patient to thereby detect said blood volume, and thereby said blood volume variation;

said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum amplitude, said maximum rate of change of said signal, said first difference, said second different, said first time interval, and said second time interval; and means for calculating the magnitude of selected ones of said parameters, said means for calculating being connected to both said means for detecting and means for measuring;

wherein the means for calculating calculates the magnitude of the mean pressure parameter in accordance with the following expression:

(1) $P'_{mi} = K_1 r_{ic}{}^a$
where
$K_1$ = calibration constant
$P'_{mi} = (P_s + P_d)/2 - P_o$
$P_{si}$ = systolic blood pressure, in cycle i
$P_{mi} = (P_s + P_d)/2$
$P_{di}$ = diastolic blood pressure, in cycle i
a = constant
$P_o$ = constant.

14. A method for determining the magnitude of heart-related parameters in a patient; comprising:

detecting blood volume, and thereby blood volume variation, in said patient and providing a signal representation of said blood volume, and thereby said blood volume variation;

said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and said minimum amplitude, a maximum rate of change of said signal being representative of the maximum rate of change of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;

measuring said maximum amplitude, said minimum amplitude, said maximum rate of change of said signal, said first difference, said second difference, said first time interval, and said second time interval; and calculating the magnitude of mean pulse pressure in accordance with the following expression:

(1) $P_{mi} = K_1 r_{ic}{}^a$
where
$K_1$ = calibration constant
$P'_{mi} = (P_s + P_d)/2 - P_o$
$P_{si}$ = systolic blood pressure, in cycle i
$P_{mi} = (P_s + P_d)/2$
$P_{di}$ = diastolic blood pressure, in cycle i
a = constant
$P_o$ = constant.

15. Apparatus for determining the magnitude of heart-related parameters in a patient; comprising;

means for detecting blood volume, and thereby blood volume variation, in said patient, and for providing a signal representative of said blood volume, and thereby said blood volume variation;

said means for detecting being attachable to said patient to thereby detect said blood volume, and thereby said blood volume variation;

said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said minimum amplitude and said maximum amplitude, a maximum rate of change of said signal being representative of the maximum rate of increase of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum rate of change of said signal being representative of the difference in volume between the maximum amount of blood volume and the volume at the time of maximum rate of change of said blood volume, and a pulse repetition period;

means for measuring said maximum amplitude, said minimum amplitude, said maximum rate of change of said signal, said first difference, said second different, said first time interval, and said second time interval; and means for calculating the magnitude of selected ones of said parameters, said means for calculating being connected to both said means for detecting and means for measuring;

wherein the means for calculating calculates implicitly the magnitude of the mean pulse pressure in accordance with the following expression:

$$K_3 1 \frac{e^{-k(P_{mo}-j\phi_{1i})} - e^{-k(P_{mo}+\phi_{2i})}}{e^{-k(P_{mo}-\phi_{1i})} - e^{-k(P_{mo}+\phi_{2i})}} = r_i \quad (3)$$

where
$P_{mo}$ = constant at calibration
$\phi_{1i} + \phi_{2i} = PP_i$ = pulse pressure during cycle i
k = constant
j = constant
$P_{si} = P_{mo} + \phi_{2i} + P_o$
$P_{di} = P_{mo} - \phi_{1i} + P_o$
$P_{mi} = (P_{si} + P_{di})/2$
$P_o$ = constant
$r_i$ = ratio of exponentials
$K_3$ = coefficient (variable or constant).

16. A method for determining the magnitude of heart-related parameters in a patient;

comprising:

detecting blood volume, and thereby blood volume variation, in said patient and providing a signal representative of said blood volume, and thereby said blood volume variation;

said blood volume variation being cyclic in nature whereby said signal comprises a cyclic curve having, in each cycle of variation, a variable slope, a maximum amplitude representative of the maximum amount of blood volume, a minimum amplitude representative of the minimum amount of blood volume, a first time interval between said maximum amplitude and the said minimum amplitude, a maximum rate of change of said signal being representative of the maximum rate of change of blood volume, a second time interval between the minimum amplitude and the time of the maximum rate of change of said signal, a first difference in amplitude between said maximum amplitude and said minimum amplitude, a second difference in amplitude between the maximum amplitude and the amplitude at the time of maximum change of rate of said signal being representative of the difference in volume between the maximum amount of blood volume and the volume at the time of maximum rate of change of said blood volume, and a pulse repetition period;

measuring said maximum amplitude, said minimum amplitude, said maximum rate of change of said signal, said first difference, said second difference, said first time interval, and said second time interval; and wherein the means for calculating calculates implicitly the magnitude of mean pulse pressure in accordance with the following expressure:

$$K_3 \frac{e^{-k(P_{mo}-j\phi_{1i})} - e^{-k(P_{mo}+\phi_{2i})}}{e^{-k(P_{mo}-\phi_{1i})} - e^{-k(P_{mo}+\phi_{2i})}} = r_i \quad (3)$$

where
$P_{mo}$ = constant at calibration
$\phi_{1i} + \phi_{2i} = PP_i$ = pulse pressure during cycle i
k = constant
j = constant
$P_{2i} = P_{mo} + \phi_{2i} + P_o$
$P_{di} = P_{mo} - \phi_{1i} + P_o$
$P_{mi} = (P_{si} + P_{di})/2$
$P_o$ = constant
$r_i$ = ratio of exponentials
$K_3$ = coefficient (variable or constant).

* * * * *